(12) United States Patent
Rowley et al.

(10) Patent No.: US 7,824,479 B2
(45) Date of Patent: Nov. 2, 2010

(54) APPARATUS AND METHOD FOR AIR SAMPLING

(75) Inventors: John Arthur Rowley, Potters Bar (GB); Derrick Robert Crump, St Albans (GB); Andrew Charles Dengel, Flitwick (GB)

(73) Assignee: Building Research Establishment Ltd., Watford (GB)

( * ) Notice: Subject to any disclaimer, the term of this patent is extended or adjusted under 35 U.S.C. 154(b) by 211 days.

(21) Appl. No.: 11/865,614

(22) Filed: Oct. 1, 2007

(65) Prior Publication Data

US 2008/0202332 A1    Aug. 28, 2008

(30) Foreign Application Priority Data

Feb. 27, 2007    (GB) ................. 0703766.6

(51) Int. Cl.
*B01D 53/02*    (2006.01)

(52) U.S. Cl. .............. 96/114; 96/108; 96/109; 96/113; 95/1; 95/11; 95/26

(58) Field of Classification Search ......... 95/1, 95/11, 26; 96/108, 109, 113, 114
See application file for complete search history.

(56) References Cited

U.S. PATENT DOCUMENTS

| | | | |
|---|---|---|---|
| 3,710,557 | A | 1/1973 | Couchman et al. |
| 4,569,253 | A | 2/1986 | Higashi et al. |
| 4,584,887 | A | 4/1986 | Galen |
| 4,765,193 | A | 8/1988 | Holden et al. |
| 4,786,472 | A | 11/1988 | McConnell et al. |
| 4,869,117 | A | 9/1989 | McAndless et al. |
| 5,047,073 | A | 9/1991 | Stetter et al. |
| 6,244,117 | B1 | 6/2001 | Mengel et al. |
| 6,477,906 | B1 | 11/2002 | Peterson |
| 6,632,268 | B2 * | 10/2003 | Seeley ............... 95/86 |
| 7,122,065 | B2 * | 10/2006 | Fox ................. 55/306 |

(Continued)

FOREIGN PATENT DOCUMENTS

| | | |
|---|---|---|
| CA | 1250359 | 2/1989 |
| GB | 847104 | 9/1960 |
| WO | WO 2006/062906 A1 | 6/2006 |

OTHER PUBLICATIONS

Department of Health, Committee on Toxicity, Committee on Toxicity of Chemicals in Food, Consumer Products and the Environment (non-food)—COT, Jun. 20, 2006, 3 pgs.

(Continued)

*Primary Examiner*—Robert J Hill, Jr.
*Assistant Examiner*—Christopher P Jones
(74) *Attorney, Agent, or Firm*—Christie, Parker & Hale, LLP

(57) ABSTRACT

An apparatus for sampling air in an aircraft cabin comprises: a sensor 2 for detecting air contaminants, a processor 4, a data logger 6, means 8 for detecting when the apparatus is airborne, a control unit 10, a manual trigger 12, at least one adsorbent tube 18, valves 14, 16 or other means for isolating the adsorbent tube from contamination and a pump 20 for drawing air through the adsorbent tube. An alternative apparatus uses a Tedlar® bag. Methods of sampling air and uses of the apparatus are also disclosed.

20 Claims, 2 Drawing Sheets

U.S. PATENT DOCUMENTS

| | | | |
|---|---|---|---|
| 7,264,648 B1 * | 9/2007 | Wetzel et al. | 95/8 |
| 2003/0067393 A1 | 4/2003 | Albro et al. | |
| 2005/0183575 A1 | 8/2005 | Fox | |
| 2005/0210957 A1 * | 9/2005 | Tipler et al. | 73/37 |
| 2008/0229805 A1 * | 9/2008 | Barket et al. | 73/31.01 |

OTHER PUBLICATIONS

Bre, Standalone capture device for measuring transient incidents on board aircraft, Jun. 2, 2006, 2 pgs.

Draft Paper for Discussion, Committee on Toxicity of Chemicals in Food Consumer Products and the Environment (COT), TOX/2006/21, 33 pgs.

British Search Report, dated Jun. 14, 2007, corresponding to GB 0703766.6.

UK Search Report, dated Jan. 29, 2008, corresponding to priority application No. GB0703766.6, listing the references cited in this IDS, except US 4,584,887, US 2005/0183575 and WO 2006/062906 A1, which were previously cited in an IDS dated Oct. 1, 2007.

* cited by examiner

APPARATUS AND METHOD FOR AIR SAMPLING

CROSS-REFERENCE TO RELATED APPLICATION(S)

This application claims priority of British Patent Application Number GB 0703766.6, filed on Feb. 27, 2007.

BACKGROUND OF THE INVENTION

The present invention relates to an apparatus and method for air sampling. In particular, it relates to an apparatus and method for air sampling in a cabin and/or flight deck of an aircraft

DESCRIPTION OF RELATED ART

When airborne, air for the cabin of an aircraft is drawn from the engine compressors of the aircraft. Occasionally, an incident occurs whereby there is a leakage of oil or hydraulic fluid. For example, a seal may leak and engine oil escapes. As a consequence of the high temperature and high pressure in the engine environment, escaped engine oil or its decomposition products may be introduced to the aircraft cabin. These processes can produce, amongst others, airborne semi-volatile organic compounds (SVOCs) and volatile organic compounds (VOCs). The semi-volatile organic compounds can include organophosphates.

SUMMARY

The present invention seeks to provide an apparatus and method for collecting particulate matter and chemical pollutants in the air, particularly in the air of an aircraft cabin.

According to the present invention there is provided an apparatus for air sampling comprising: at least one adsorbent tube; means for isolating the adsorbent tube from contamination; and means for drawing air through the adsorbent tube.

Preferably the apparatus further comprises means for recording operating data. It may further comprise means for controlling the activation of the means for drawing air through the adsorbent tube.

The apparatus may be adapted to be manually actuated when contaminated air is sensed by smell or sight. Alternatively, it may comprise means for sensing air contamination. The apparatus may comprise a processor for receiving information from the sensing means and determining when contamination has occurred.

Preferably, the apparatus comprises means for detecting when the apparatus is airborne. The detecting means may be an altimeter or a pressure transducer.

The apparatus may comprise means for controlling when the adsorbent tube is isolated. This control means may also be the means for controlling the activation of the means for drawing air through the adsorbent tube.

In one embodiment, the adsorbent tube has an inlet and an outlet, these being openable and closeable, wherein the adsorbent tube is isolated when the inlet and outlet are closed. The isolation control means may control the opening and closing of the adsorbent tube.

Preferably the apparatus comprises means for drawing air into the adsorbent tube.

Preferably, the adsorbent tube is adapted to capture volatile and/or semi-volatile organic compounds. The adsorbent tube may be a stainless steel adsorbent tube containing an appropriate adsorbent. Preferably, the apparatus comprises a plurality of adsorbent tubes, one or more of these tubes being used sequentially as incidents of contaminated air arise. When an incident arises, a pair of adsorbent tubes may be used.

In one embodiment, the apparatus further comprises a TEDLAR® bag (a polyvinyl fluoride film made by DuPont) to capture a sample of air. The TEDLAR bag is preferably connected to the adsorbent tube such that air flows from the TEDLAR bag into the adsorbent tube.

The apparatus may further comprise a unit comprising polyurethane foam. The unit may also comprise a particle filter. Preferably, the unit comprises a plurality of air sampling conduits that are used sequentially. The unit may be rotatable.

The apparatus is preferably a stand-alone unit. It is therefore able to operate in a self-sufficient way, obviating the need for an operator onboard an aircraft or the need to use power from an aircraft's electrical system.

According to the present invention, there is also provided a method of sampling air comprising the following steps:
a) detecting contamination of the air;
b) passing contaminated air through an adsorbent tube; and
c) recording the time that air passes through the adsorbent tube.

The method preferably comprises, prior to step (a), sensing when the adsorbent tube is airborne.

The method may comprise, prior to step (b), passing contaminated air into a TEDLAR bag.

The method may further comprise passing contaminated air through polyurethane foam.

Preferably, the method comprises automatically using another adsorbent tube when contaminated air is next detected.

In one embodiment, prior to step (b), the method comprises opening an adsorbent tube. After step (b), the method may comprise closing an adsorbent tube.

The apparatus and method of the present invention are preferably for use on an aircraft for sampling cabin air. They can be used to monitor the performance of an aircraft engine, for example by detecting oil leaks and other events that cause air contamination. They can also be used to certify the performance of new or existing systems for monitoring the quality (eg. by detecting contamination) of cabin air.

BRIEF DESCRIPTION OF THE DRAWINGS

Embodiments of the present invention will now be described, by way of example only, with reference to the accompanying diagrammatic drawings, in which.

DETAILED DESCRIPTION

Figure 1:
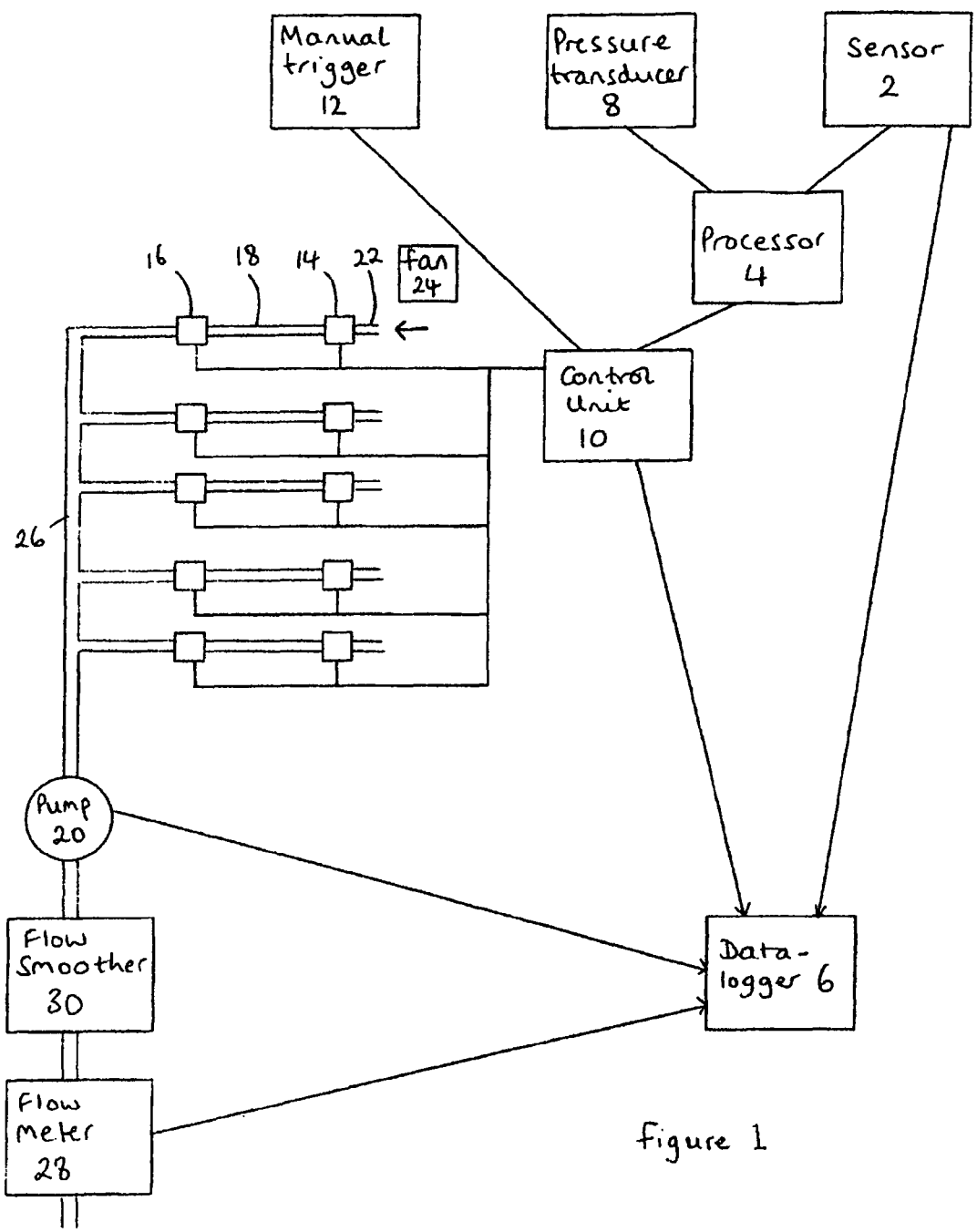
FIG. 1 is a schematic diagram of one embodiment of the present invention.

Referring to FIG. 1, the apparatus of the present invention is located in an aircraft cabin and comprises a sensor 2 for detecting air contaminants such as ultrafine particles (e.g. smoke) and/or carbon monoxide. The sensor operates when an incident of oil leakage occurs and cabin air is thereby contaminated. As an example, ultrafine particle sensors detect particles having a size of less than 1 micrometer. Generally, when these particles are detected by a sensor, there is an increase in voltage, and a corresponding electrical signal is sent to a processor 4. The sensor is set up so that its signal can be recorded by a data logger 6.

A forward light scattering sensor may be used, whereby a laser beam is diffracted by a small angle by the smoke particles. An example is a Stratos-Micra 25 sensor which is available from AirSense Technology Ltd, UK. The Stratos-Micra is an air sampling smoke detector. It has a particle sensitivity range specified of 0.003 to 10 micrometers (although for airborne particles a range of 0.3 to 10 micrometers is more likely).

An alternative sensor is an ionisation smoke detector which operates as follows. When a small sample of air is ionised by means of a radioactive substance, the ions allow a small electrical current to flow between two electrodes placed in the sample. If smoke contaminates the air in the sample then the smoke inhibits the movement of the ions and the electrical current decreases. A suitable ionisation smoke detector (Series 65) is available from Apollo Fire Detectors Ltd, UK.

Another suitable sensor is a Cirrus ProLoctor which is based on a Cloud Chamber Detection principle. It is available from Safe Fire Detection Inc of the USA.

Another alternative is a TSI P-Trak™ Ultrafine Particle Counter from TSI Incorporated of the USA, which is based on a condensation nucleus counter. Here the particles are initially passed through a saturated vapour of propanol. This condenses on to them so that they grow to a size sufficiently large for them to scatter light and thus be measured by a focused laser light source and a photo detector.

Preferably, the apparatus of the present invention functions as a stand-alone unit and can be operated by a DC storage battery, for example. Thus, the sensor is preferably operational at low power or can be modified to be operational at low power. As an alternative to being a stand-alone unit, the apparatus can be connected to the electrical circuitry of an aircraft in which it is located.

When an aircraft is on the ground, the air both inside and outside the aircraft can be contaminated by particulate matter and chemical pollutants. This is caused, for example, by refueling of the aircraft or by the engines of adjacent vehicles. Thus, the sensor is preferably switched off when the aircraft is on the ground. In one embodiment, the sensor is switched on manually once the aircraft is sufficiently high in the air. However, in a preferred embodiment, means are provided for detecting when the apparatus is airborne. In the present embodiment, this means is a pressure transducer 8, although an altimeter could also be used, for example.

In an alternative embodiment, the sensor is activated on the ground and the processor 4 monitors the output of the sensor and is able to detect, by tracing the ultrafine particles detected by the sensor, when the aircraft has left the ground. In this respect, the levels of ultrafine particles detected by the sensor decrease when the aircraft is airborne since the aircraft is away from the contaminated air near the ground; the ultrafine particle level only increases for a minute or so when an incident of oil leakage, and therefore air contamination, occurs.

In one embodiment, no sensor is required. Instead the apparatus relies on someone within the cabin smelling or seeing smoke and switching on a control unit 10 using a manual trigger 12.

When running in automatic mode, the processor 4 contains a small circuit which monitors the output from the sensor and determines when an incident of air contamination has occurred. This information is passed electronically to the control unit 10. The control unit opens an inlet valve 14 and an outlet valve 16 of an adsorbent tube 18. It therefore opens and closes the adsorbent tube. It also switches on a pump 20 for drawing air through the adsorbent tube. The control unit controls the sequencing and sampling: it regulates the taking of samples and the use of the adsorbent tubes. The control unit records the sampling time, i.e. the time when the adsorbent tube is open, by recording, for example, when sampling starts and its duration. It also monitors how many tubes have been used and therefore when they need replacing.

When an incident of air contamination arises, this is detected, preferably by the sensor, and the control unit effects the drawing of air into the apparatus of the present invention from the cabin. Inlet tubing 22 is used to transfer the cabin air into the apparatus. A fan 24 may be used to draw the air into the system via the inlet tubing.

The apparatus of the present invention comprises five adsorbent tubes, although fewer than five tubes, or more than five tubes, may be used instead. One end of each adsorbent tube is connected to the inlet valve 14. The inlet valve is connected to the inlet tubing 22. The inlet valve isolates the apparatus from the cabin air until air contamination is detected and an air sample needs to be drawn through the tube. The inlet valve is chosen so as not to absorb or otherwise remove the ultrafine particles and/or chemical pollutants in the air that require collection. The valve is also inert to these ultrafine particles/chemical pollutants.

The inlet valve 14 may be a solenoid valve. A suitable solenoid valve is manufactured by Burkert Contromatic Limited of UK (e.g. item number 137754W). It is a 2/2-way valve, normally closed, which has an NPT (national pipe thread size) ⅛ fitting and a PVDF (polyvinylidine di-fluoride) valve body.

The inlet valve is connected to a stainless steel adsorbent tube, which is normally closed to the environment using its inlet valve 14 and outlet valve 16. Suitable adsorbent tubes are available from PerkinElmer, Inc of the USA or Markes International of the UK, for example. The inside of the tube contains suitable sorbent material to capture volatile organic compounds and semi-volatile organic compounds. A sample of contaminated air arising from an incident of oil leakage, for example, passes through a single adsorbent tube. Alternatively, when an incident of oil leakage occurs, samples of contaminated air pass through a pair of adsorbent tubes such that the particles and compounds captured by one tube can be experimentally confirmed by the particles and compounds captured by the other tube. The remote end of each adsorbent tube is attached to the outlet valve 16 which is again selected so as to be inert. A high flow rate of air through these adsorbent tubes is possible.

Air for sampling is drawn through the adsorbent tube(s) and the valves using pump 20. The pump is connected to the adsorbent tubes using connecting tubes 26. The pump is a conventional air sampling pump; it operates under the varying pressure of a cabin environment. Preferably, a flow meter 28 is present to monitor the working of the pump and, if necessary, a flow smoother 30 is used.

As alternatives to inlet valve 14 and outlet valve 16, other means for isolating the adsorbent tube from contamination, in particular air-borne contamination, may be used. For example, a diffusion limiting cap can be used in place of inlet valve 14 to prevent ingress of contaminants when sampling is not occurring. A suitable diffusion limiting cap is manufactured by Markes International under the name Safelok. The adsorbent tubes could also be contained within a carousel mechanism such that the tubes are sealed against a metal plate when not in use. When required, the carousel would rotate to position an adsorbent tube such that the airflow from the inlet tubing 22 to the connecting tubing 26 flowed through the adsorbent tube.

From the data recorded by the apparatus, the volume of air sampled is known, such that the concentration of collected compounds in the air sample can be calculated. The flow meter is useful in determining the sampling volume since it sets a time and rate for the pump.

The data logger records information as necessary when the unit is operational.

The electrical connections required between the different units of the apparatus are shown schematically in FIG. 1. A voltage increase originating from the sensor when air contaminants are detected triggers the apparatus into an 'alarm' state.

In operation, a blank sample may be collected: i.e. a sample of uncontaminated cabin air for reference purposes.

Once the aircraft is airborne and the sensor detects ultrafine particles and/or carbon monoxide, cabin air is drawn into an adsorbent tube such that organic compounds contained in the air sample can be collected by the adsorbent tube. After a preset time, the apparatus switches into rest mode awaiting a further incident. When a further incident arises, the control unit ensures that an unused adsorbent tube is used to collect the next sample of contaminated air. The control unit, registers when all the adsorbent tubes have been used to collect air samples. A signal can then be generated to alert users to the fact that the adsorbent tubes require replacing.

The apparatus is designed as a stand-alone discrete unit. It is preferably designed so that people within the cabin are not aware of its purpose or even its presence. The apparatus is designed for quick sampling since the air may only be contaminated for a minute or so.

Figure 2:
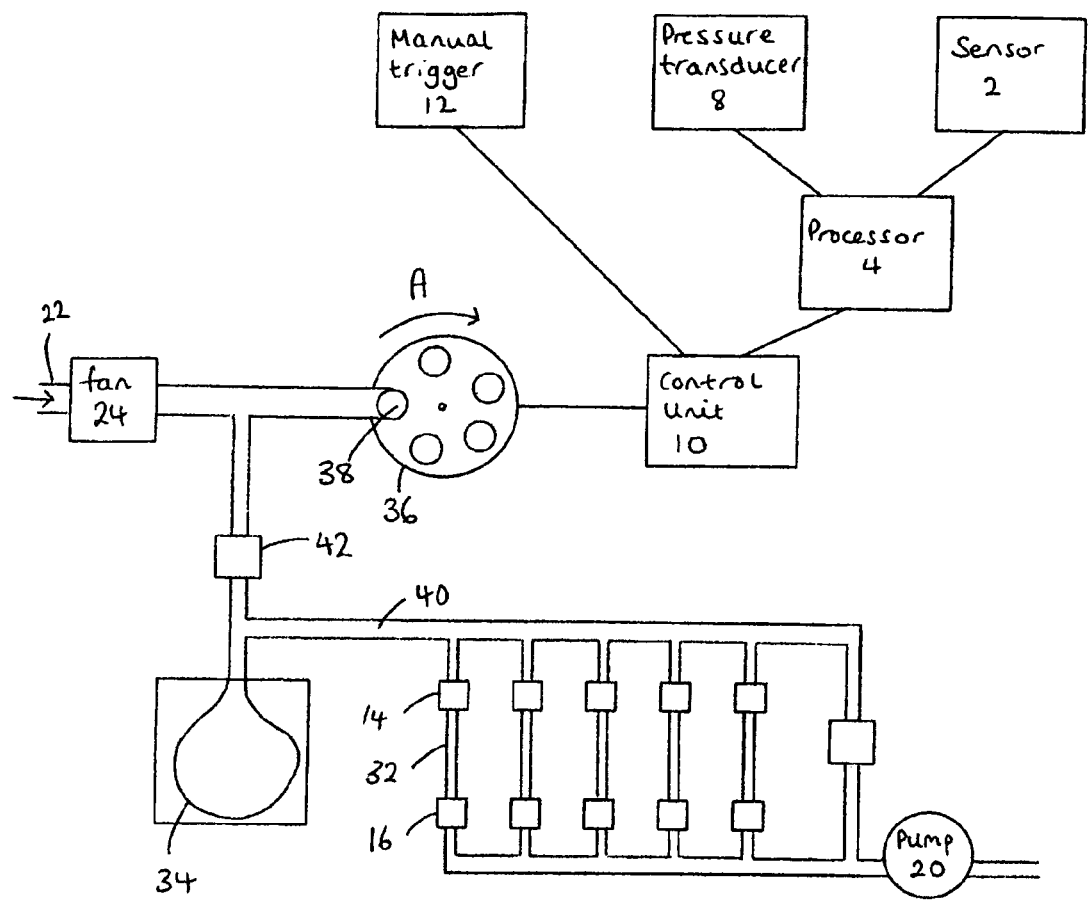
FIG. 2 is a schematic diagram of an alternative embodiment of the present invention.

Referring to FIG. 2, alternative apparatus for detecting and sampling contaminated air is shown schematically. In accordance with the embodiment shown in FIG. 1, the embodiment of FIG. 2 comprises a sensor 2, a pressure transducer 8, a processor 4, a manual trigger 12 and a control unit 10. It also has a pump 20 for drawing air through adsorbent tubes 32. A series of adsorbent tubes 32 is used, in accordance with the first embodiment described.

The apparatus of FIG. 2 also comprises a TEDLAR® Bag 34, available from companies such as SKC Ltd, that is able to collect a large volume of air in a short period of time. Air from the TEDLAR bag is passed via tubing 40 to one or more adsorbent tubes, generally at a slower flow rate.

The apparatus includes a filtering unit 36. The unit shown is cylindrical in shape and is adapted to rotate in direction A about a central, longitudinal axis. The unit shown has five isolated conduits or tubes 38, each being cylindrical in shape and having their longitudinal axes parallel to the axis of the filtering unit. Each tube 38 is manufactured from a material that will not interfere with the collection of semi-volatile organic compounds, such materials including aluminium alloy and stainless steel. The tubes are of a suitable diameter and length to hold a 65 mm diameter polyurethane foam plug for the collection of semi-volatile organic compounds such as that described in US Environmental Protection Agency method TO-4A.

In one embodiment the front of each filtering unit tube has a quartz or glass fibre filter on its front face to trap ultrafine particles in the air. Valves are used to isolate the filtering unit tube from environmental air, thereby keeping the polyurethane foam uncontaminated until a polluted air sample passes therethrough.

One sample of air is collected by a single filtering unit tube each time an incident of oil leakage occurs. Thus, in the filtering unit shown, semi-volatile organic compounds can be collected as a result of five separate incidents, although this can be increased or decreased to any required number by increasing or decreasing the number of tubes 38 accordingly. The filtering unit rotates about its central axis so that one tube is usable after another.

When an incident of air contamination arises, air is drawn into the apparatus of FIG. 2 from the cabin. Inlet tubing 22 is used to transfer the cabin air into the apparatus. A fan 24 is used to draw the air into the system via the inlet tubing. This provides sufficient back pressure for the air to inflate a TEDLAR bag over the period of time that the fan is in operation.

The air drawn into the apparatus is divided at a T-junction in the tubing. Some of the air flows, via tubing aligned with the relevant filtering unit tube, into a tube 38 of the filtering unit 36. The polyurethane foam in the tube absorbs the semi-volatile organic compounds from the air sample.

The rest of the cabin air passes along an alternative route through a valve 42 into a TEDLAR bag. This bag collects a large volume of air in a short time. After a preset time, the valve 42 is closed and the pump 20 draws the air from the TEDLAR bag through the appropriate adsorbent tube. Once a sufficient volume of air has passed through the adsorbent tube, the valve is by-passed to fully deflate the TEDLAR bag. The pump 20 draws the air out of the TEDLAR bag and into the adsorbent tube at a relatively low flow rate, as appropriate for the adsorbent tube. The rate of the pump and the time for which it is operational is monitored so that the volume of air passing through the tube can be determined.

Preferably, once a TEDLAR bag has been used, it can either be cleaned by flushing it with nitrogen or it may form one of a series of TEDLAR bags, such that, once one TEDLAR bag has been used, a clean one is aligned for subsequent use. The adsorbent tubes 32 are used in the same way as described above in relation to the first embodiment of the invention. In one embodiment, a separate TEDLAR bag is connected to a single tube or a pair of tubes, depending on whether an air sample relating to one incident is collected by a single tube or a pair of tubes.

In the embodiments described, the apparatus is constructed to sample contaminated air on five separate occasions. It will be appreciated that the apparatus can be adapted to take air samples on less than five occasions or more than five occasions. The maximum number of occasions in which air samples can be taken is dictated by the number of adsorbent tubes available, since at least one adsorbent tube is required for each new incident of air contamination. Preferably, a plurality of adsorbent tubes are present which are used sequentially as incidents arise.

Once the adsorbent tubes have been used to absorb the semi-volatile and volatile organic compounds arising from an incident, the tubes can be taken away for analysis of their contents to confirm that there is a problem of oil leakage.

The invention claimed is:

1. An apparatus for air sampling comprising:
   at least one adsorbent tube;
   means for isolating the adsorbent tube from contamination;
   means for sensing air contamination;
   a processor for receiving information from the sensing means and determining when contamination has occurred;
   means for drawing air through the adsorbent tube upon the processor determining that contamination has occurred; and
   means for detecting when the apparatus is airborne and initiating the means for drawing air through the adsorbent tube upon determining that the apparatus is airborne.

2. Apparatus as claimed in claim 1, further comprising means for recording operating data.

3. Apparatus as claimed in claim 1, further comprising means for controlling the activation of the means for drawing air through the adsorbent tube.

4. Apparatus as claimed in claim 1, which is adapted to be manually actuated when contaminated air is sensed by smell or sight.

5. Apparatus as claimed in claim 1, wherein the detecting means is an altimeter or a pressure transducer.

6. Apparatus as claimed in claim 1, further comprising means for controlling when the adsorbent tube is isolated.

7. Apparatus as claimed in claim 1, wherein the adsorbent tube has an inlet and an outlet, these being openable and closeable, wherein the adsorbent tube is isolated when the inlet and outlet are closed.

8. Apparatus as claimed in claim 1, further comprising means for drawing air into the adsorbent tube.

9. Apparatus as claimed in claim 1, wherein the adsorbent tube is adapted to capture volatile and/or semi-volatile organic compounds.

10. Apparatus as claimed in claim 1, further comprising a bag made of polyvinyl fluoride film to capture a sample of air.

11. Apparatus as claimed in claim 10, wherein the bag is connected to the adsorbent tube such that air flows from the bag into the adsorbent tube.

12. Apparatus as claimed in claim 1, further comprising a filtering unit through which a sample of air is drawn.

13. Apparatus as claimed in claim 12, wherein the filtering unit comprises a polyurethane foam plug.

14. Apparatus as claimed in claim 12, wherein the filtering unit comprises a plurality of air sampling conduits that are used sequentially.

15. Apparatus as claimed in claim 14, wherein the filtering unit is rotatable.

16. Apparatus as claimed in claim 1, wherein the adsorbent tube is a stainless steel adsorbent tube containing an appropriate adsorbent.

17. Apparatus as claimed in claim 1 comprising a plurality of adsorbent tubes, one or more of these tubes being used sequentially as incidents of contaminated air arise.

18. Apparatus as claimed in claim 17, wherein when an incident arises, a pair of adsorbent tubes is used.

19. Apparatus as claimed in claim 1 that is a stand-alone unit.

20. A method of using the apparatus as claimed in claim 1 on an aircraft for sampling cabin air, the method comprising:
- initiating operation of the sensing means upon the detecting means detecting that the apparatus is airborne; and
- drawing air through the adsorbent tube upon the processor determining that contamination has occurred.

* * * * *